United States Patent [19]
Bhattacharya

[11] Patent Number: 4,605,760
[45] Date of Patent: Aug. 12, 1986

[54] PREPARATION OF AN ENANTIOMER OF A SUBSTITUTED FLUORENYLOXYACETIC ACID

[75] Inventor: Apurba Bhattacharya, Rahway, N.J.

[73] Assignee: Merck & Co., Inc., Rahway, N.J.

[21] Appl. No.: 766,376

[22] Filed: Aug. 16, 1985

[51] Int. Cl.$^4$ ............................................. C07C 69/94
[52] U.S. Cl. .................................... 562/461; 568/327; 560/53
[58] Field of Search ......................... 562/461; 568/327

[56] References Cited

U.S. PATENT DOCUMENTS

| | | | |
|---|---|---|---|
| 3,704,314 | 11/1972 | Cragoe et al. | 562/461 |
| 3,903,145 | 9/1975 | Levine et al. | 562/461 |
| 4,070,539 | 1/1978 | Cragoe et al. | 562/461 |
| 4,316,043 | 2/1982 | Cragoe et al. | 562/461 |
| 4,317,922 | 3/1982 | Cragoe, Jr. | 562/461 |

Primary Examiner—Paul J. Killos
Attorney, Agent, or Firm—Daniel T. Szura; Charles M. Caruso; Hesna J. Pfeiffer

[57] ABSTRACT

A process for direct preparation of an enantiomer of a substituted fluorenyloxyacetic acid is disclosed. The acetic acid derivative is useful for treating brain edema.

10 Claims, No Drawings

PREPARATION OF AN ENANTIOMER OF A SUBSTITUTED FLUORENYLOXYACETIC ACID

BACKGROUND OF THE INVENTION

The invention is principally concerned with a process for direct preparation of enantiomers of a substituted fluorenyloxyacetic acid.

Certain fluorenyloxyacetic acids useful for treating brain edema are disclosed in U.S. Pat. No. 4,316,043. These acetic acids have a chiral center and exist as racemic mixtures, racemates and individual isomers.

A process has been discovered for directly preparing individual isomers of a fluorenyloxyacetic acid.

SUMMARY OF THE INVENTION

A process for preparing an isomer of a substituted fluorenyloxyacetic acid.

DETAILED DESCRIPTION OF THE INVENTION

An embodiment of the present invention is a process for preparing the (+) isomer of a compound having the formula:

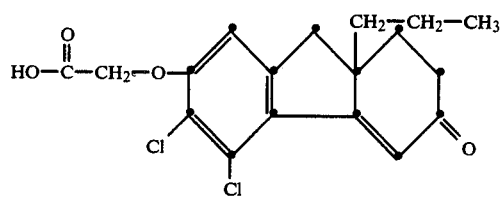

which comprises:

a. treating a compound of the formula:

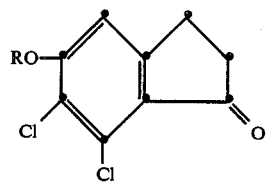

with

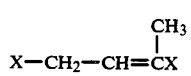

wherein X is Cl or Br and R is $C_1$-$C_6$-alkyl in a basic medium to obtain:

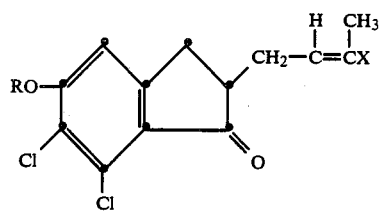

b. treating III with $C_3H_7$—X in the presence of a chiral catalyst to obtain:

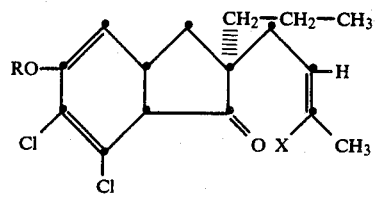

rich in the (−) isomer.

c. crystallizing IV to obtain pure (−) isomer, i.e., (−) isomer substantially or completely free of (+) isomer, d. treating the IV isomer from (c) with $NaNO_2$ in an aprotic solvent or LiCl in N-methylpyrrolidinone to obtain:

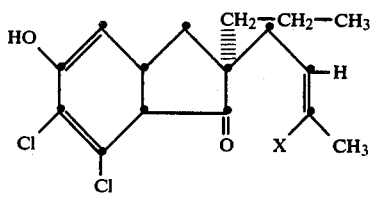

e. alkylating V to obtain:

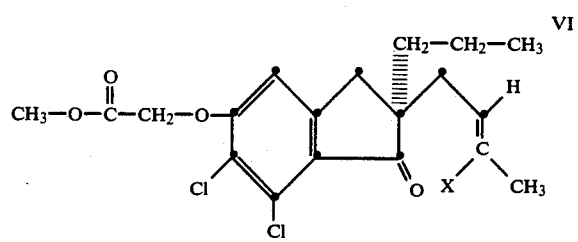

f. treating VI with $H_2SO_4/CH_2Cl_2$ to obtain:

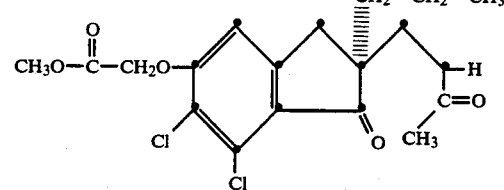

and go treating VII with a base to obtain I.

The compound VI is useful for treating brain edema as described in U.S. Pat. No. 4,316,043.

Any suitable chiral catalyst may be used such as N-aryl cinchoninium halide wherein aryl is substituted or unsubstituted phenyl or pheny-$C_1$-$C_4$-alkyl, wherein substituents (1 or 2) are selected from $CF_3$, halo, $C_1$-$C_3$alkyl, $OCH_3$, CN, and the like. Preferred catalysts are 3,4-dichlorobenzyl cinchoninium chloride and p-trifluoromethyl benzyl cinchoninium bromide. Using these type catalysts, formula IV compound containing the (−) isomer predominantly is obtained; the ratio of (−):(+) isomer will range from 75:25 to 80:20 or higher.

Step (a) involves alkenylation of the racemic formula II substituted indanone with a formula IIa haloalkene in a basic medium. The basic medium is generally an aqueous strong base, e.g. KOH, NaOH, etc. A nonaqueous solvent is also required. This solvent may be any suitable hydrocarbon such as benzene, toluene, an alkane, mixtures thereof and the like. The step (a) reaction is conveniently carried out at atmospheric pressure and at temperatures ranging from about 0° C. to about 30° C., and preferably at room temperature.

The formula III product from step (a) is obtained as a racemic mixture.

Compound III is then alkylated in step (b) in the presence of the aforesaid chiral catalyst to obtain compound IV rich in the (−) isomer.

The IV compound is obtained a mixture rich in the (−) isomer. This mixture is subjected to crystallization from a suitable hydrocarbon solvent such as hexane-and substantially pure (−) isomer of IV is obtained.

The ether group OR in IV is then cleaved to obtain V having the —OH group using conventional procedures, e.g. by treatment with $NaNO_2$ in an aprotic solvent or with LiCl in N-methylpyrrolidinone (NMP).

Compound V is alkylated using conventional reagents illustrated by β-haloacetic acid ester/KI/$Na_2CO_3$. The alkylated derivative VI is then treated with $H_2SO_4/CH_2Cl_2$ to produce the formula VII dione.

The formula VII dione as then treated with a strong base such as NaOH, KOH, LiOH, $Na_2CO_3$ and the like to obtain the formula I product.

The following example illustrates the process of the present invention. All temperatures are in °C. unless otherwise indicated.

EXAMPLE 1

Step A. Preparation of 6,7-dichloro-2-(3-chloro-2-butenyl)-2,3-dihydro-5-methoxy-1-inden-1-one 1b 1b was prepared from indanone 1 following Negishi's method [J. Org. Chem. 1983, 48, 2427–2430].

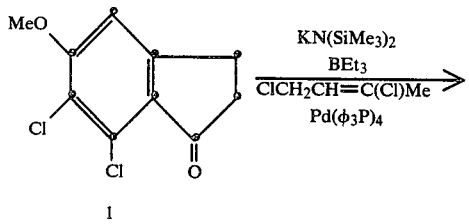

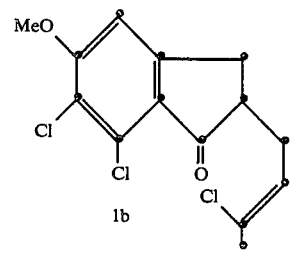

Indanone 1: 2.1951 g (9.5026 mm)
$KN(SiMe_3)_2$: 16.9 ml of 0.6M solution (10.16 mm)
1,3-dichloro-2-butene: 1.2751 g (10.2 mm)
$Pd(\phi_3P)_4$: 1 g (0.87 mm)
$Et_3B$: 10.2 ml of 1M solution (10.2 mm)

The indanone 1 was added to 10 ml dry THF in a 100 ml 3-neck flask equipped with $N_2$-inlet and magnetic stirring. To this suspension was slowly added the $KN(SiMe_3)_2$ solution in toluene (about 20 minutes) at −78° [dry ice-acetone cooling]. Solution occurred; it was stirred at −78° for 30 minutes. After 30 minutes triethylborane solution in THF was slowly added (about 10 minutes) to this mixture at −78°. The solution was warmed up to 0°. A clear solution thus formed was added to a mixture of 1,3-dichloro-2-butene and $Pd(\phi_3P)_4$ in 20 ml THF kept at 0° under $N_2$. The mixture was stirred for 12 hours at room temperature and was treated with 50 ml, 2N HCl. The organic layer was separated and the aqueous layer was extracted with 3×20 ml $CH_2Cl_2$. The combined organic layer was washed with 1N $NaHCO_3$ solution and dried over $MgSO_4$ (6 g). After removal of the solvent under vacuum, off white colored solid crystals were obtained. These solid-crystals were washed with 10 ml hexane, filtered and dried to yield 2.73 g of 1b (90%). This was used in the next reaction without further purification.

Step B: Preparation of 2b

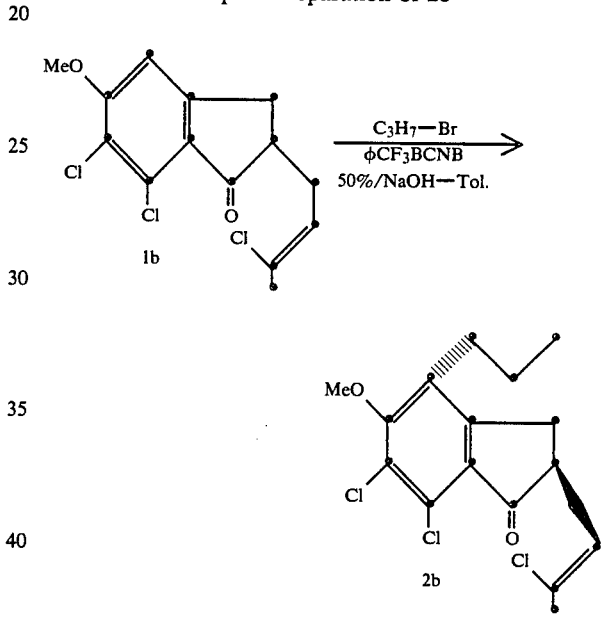

Indanone (1b): 0.3352 g (1.049 mm)
Toluene: 18 ml
50% NaOH: 3 ml
1-Bromopropane: 5.85 ml
$pCF_3$ benzylcinchoninium bromide (catalyst): 0.05 g (0.09 mm)

A 100 ml 3-neck flask fitted with magnetic stirring and $N_2$-inlet was charged with indanone 1b (0.3352 g), toluene (18 ml), 1-bromopropane (5.85 ml) and catalyst (φCF₃BCNB) (0.05 g). To this suspension at room temperature was added slowly 3 ml 50% NaOH via syringe (about 1 minute) under stirring. The mixture was stirred at room temperature for 24 hours. Disappearance of starting material observed by TLC. The mixture was then transferred in a separatory funnel with 30 ml isopropyl acetate and 20 ml water. Aqueous layer was discarded. The organic layer was washed with 2×20 ml 4N HCl and 1×20 ml 1N $NaHCO_3$ solution. The organic layer was dried over $MgSO_4$ (1 g) and solvent removed under vacuum to produce a yellow oil [0.379 g (99% yield)]. NMR, $CDCl_3$, tris [(3-heptafluoropropyl)hydroxymethylene)-d-camphorato]Eeuropium III analysis of this product (2b) showed it to be 80:20 (−):(+) enantiomeric ratio mixture.

Conversion of 2b to Formula I via steps (c), (d), (e), (f), and (g) is carried out as described in pending U.S. application Ser. No. 656,577 filed Oct. 1, 1984 (incorporated herein by reference).

Claims to the invention follow.

What is claimed is:

1. A process for preparing the (+) isomer of a compound of the formula:

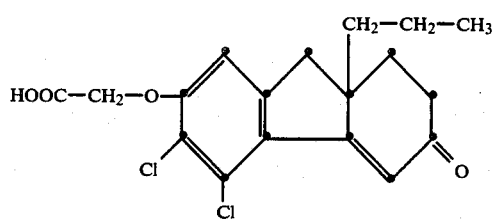

which comprises:

a. treating a compound of the formula:

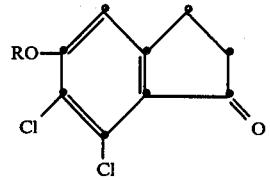

with

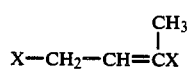

wherein X is Cl or Br and R is $C_1$-$C_6$-alkyl in a basic medium to obtain:

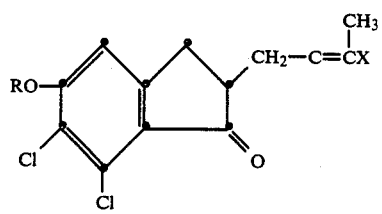

b. treating III with $C_3H_7$—X in the presence of a chiral catalyst to obtain:

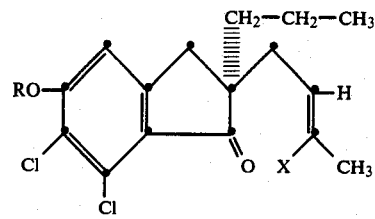

rich in the (−) isomer;

c. crystallizing IV to obtain pure (−) isomer, d. treating the IV isomer from (c) with $NaNO_2$ in an aprotic solvent or LiCl in N-methylpyrrolidinone to obtain:

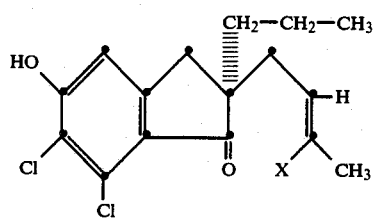

e. alkylating V to obtain:

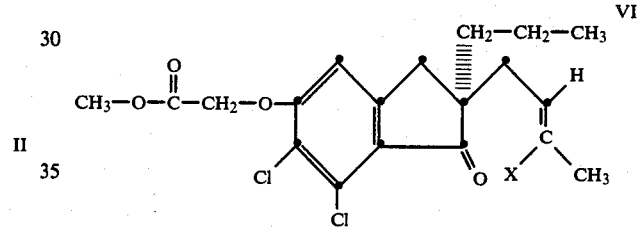

and f. treating VI with $H_2SO_4/CH_2Cl_2$ to obtain:

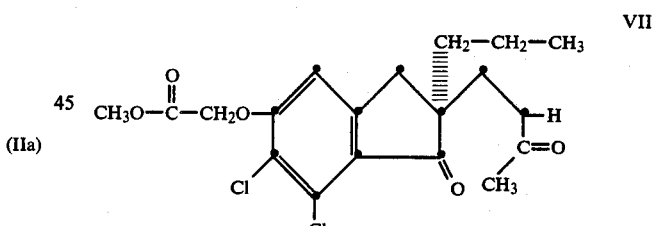

and g. treating VII with a base to obtain I.

2. The process of claim 1 wherein R is $CH_3$.

3. The process of claim 1 wherein the chiral catalyst is an aryl cinchoninium halide.

4. The process of claim 1 wherein the chiral catalyst is p-trifluoromethyl benzyl-cinchoninium bromide.

5. The process of claim 4 wherein IV is rich in the (−) isomer.

6. Step (b) of the claim 1 process.

7. The process of claim 6 wherein the chiral catalyst is an aryl cinchoninium halide.

8. The process of claim 7 wherein the chiral catalyst is p-trifluoromethyl benzyl-cinchoninium bromide.

9. The formula IV compound of claim 1 rich in the (−) isomer.

10. The formula III compound of claim 1.

* * * * *